(12) United States Patent
Friesen et al.

(10) Patent No.: US 9,768,472 B2
(45) Date of Patent: *Sep. 19, 2017

(54) SYNTHESIS OF HETERO IONIC COMPOUNDS USING DIALKYLCARBONATE QUATERNIZATION

(71) Applicant: Fluidic, Inc., Scottsdale, AZ (US)

(72) Inventors: Cody A. Friesen, Fort McDowell, AZ (US); Derek Wolfe, Scottsdale, AZ (US); Paul Bryan Johnson, Phoenix, AZ (US)

(73) Assignee: FLUIDIC, INC., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/371,028

(22) Filed: Dec. 6, 2016

(65) Prior Publication Data

US 2017/0092989 A1  Mar. 30, 2017

Related U.S. Application Data

(63) Continuation of application No. 13/526,432, filed on Jun. 18, 2012.

(60) Provisional application No. 61/569,159, filed on Dec. 9, 2011, provisional application No. 61/498,308, filed on Jun. 17, 2011.

(51) Int. Cl.
| | |
|---|---|
| *H01M 10/26* | (2006.01) |
| *H01M 4/42* | (2006.01) |
| *H01M 2/16* | (2006.01) |
| *H01M 4/38* | (2006.01) |
| *H01M 4/24* | (2006.01) |
| *H01M 4/02* | (2006.01) |

(52) U.S. Cl.
CPC ........... *H01M 10/26* (2013.01); *H01M 2/162* (2013.01); *H01M 4/244* (2013.01); *H01M 4/38* (2013.01); *H01M 2004/021* (2013.01); *H01M 2004/023* (2013.01); *H01M 2300/0014* (2013.01)

(58) Field of Classification Search
None
See application file for complete search history.

(56) References Cited

U.S. PATENT DOCUMENTS

| | | | |
|---|---|---|---|
| 3,519,631 | A | 7/1970 | Ost et al. |
| 4,034,107 | A | 7/1977 | King et al. |
| 8,481,207 | B2 | 7/2013 | Friesen |

(Continued)

FOREIGN PATENT DOCUMENTS

| | | |
|---|---|---|
| CN | 1581567 | 2/2005 |
| CN | 1946673 | 4/2007 |

(Continued)

OTHER PUBLICATIONS

European Office Action dated Dec. 1, 2016 for Appln. No. 12723975.4.

(Continued)

*Primary Examiner* — Tracy Dove

(74) *Attorney, Agent, or Firm* — Pillsbury Winthrop Shaw Pittman LLP

(57) ABSTRACT

Methods of preparing hetero ionic complexes, and ionic liquids from bisulfate salts of heteroatomic compounds using dialkylcarbonates as a primary quaternizing reactant are disclosed. Also disclosed are methods of making electrochemical cells comprising the ionic liquids, and an electrochemical cell comprising an alkaline electrolyte and a hetero ionic complex additive.

63 Claims, 2 Drawing Sheets

(56) References Cited

U.S. PATENT DOCUMENTS

| | | |
|---|---|---|
| 8,741,491 B2 | 6/2014 | Wolfe et al. |
| 9,147,919 B2 | 9/2015 | Friesen et al. |
| 2001/0038937 A1 | 11/2001 | Suzuki et al. |
| 2003/0065037 A1 | 4/2003 | Mattison et al. |
| 2004/0241537 A1 | 12/2004 | Okuyama et al. |
| 2005/0171355 A1 | 8/2005 | Kuwabara et al. |
| 2005/0194561 A1 | 9/2005 | Davis |
| 2008/0021037 A1 | 1/2008 | Beylin et al. |
| 2008/0096061 A1 | 4/2008 | Burchardt et al. |
| 2008/0251759 A1 | 10/2008 | Kalb et al. |
| 2010/0016603 A1 | 1/2010 | Sonoda et al. |
| 2010/0137460 A1 | 6/2010 | Bart et al. |
| 2010/0285375 A1 | 11/2010 | Friesen et al. |
| 2010/0323249 A1 | 12/2010 | Fujiwara et al. |
| 2011/0027664 A1 | 2/2011 | Burghardt |
| 2011/0065018 A1 | 3/2011 | Kim et al. |
| 2011/0091777 A1 | 4/2011 | Mizuno et al. |
| 2011/0152292 A1 | 6/2011 | Rayner-Branes et al. |
| 2011/0281184 A1 | 11/2011 | Friesen et al. |
| 2011/0305959 A1 | 12/2011 | Friesen et al. |

FOREIGN PATENT DOCUMENTS

| | | |
|---|---|---|
| CN | 101137436 | 3/2008 |
| CN | 101174698 | 5/2008 |
| CN | 102050788 | 5/2011 |
| EP | 1 182 196 | 2/2002 |
| EP | 1 398 318 | 3/2004 |
| GB | 1297955 | 11/1972 |
| JP | 2001-266961 | 9/2001 |
| JP | 2002-509528 | 3/2002 |
| JP | 2002-184472 | 6/2002 |
| JP | 2005 026023 | 1/2005 |
| JP | 2007-87939 | 4/2007 |
| JP | 2007-518772 | 7/2007 |
| JP | 2010-146851 | 7/2010 |
| WO | WO 2005/003108 | 1/2005 |
| WO | WO 2006/072785 | 7/2006 |
| WO | WO 2008/013095 | 1/2008 |
| WO | WO 2010/000396 | 1/2010 |
| WO | WO 2010/132357 | 11/2010 |
| WO | WO 2010136783 | 12/2010 |
| WO | WO 2011/049184 | 4/2011 |
| WO | WO 2012/111101 | 8/2012 |
| WO | WO 2012/174564 | 12/2012 |

OTHER PUBLICATIONS

European Office Action dated Dec. 2, 2016 for Appln. No. 12731837.6.
Hajipour et al., "Basic ionic liquids. A short review", Iranian Chemical Society, Journal, vol. 6, No. 4, Dec. 1, 2009, pp. 647-678.
U.S. Office Action dated Dec. 2, 2014 for U.S. Appl. No. 13/526,342.
K. Scott, Section 2—Membrane Materials, Preparation and Characterisation, In Handbook of Industrial Membranes (Second Edition), edited by K. Scott, Elsevier Science, Amsterdam, 1998, pp. 187-269, ISBN 9781856172332, http://dx.doi.org/10.1016/B978-185617233-2/50005-2. (http://www.sciencedirect.com/science/article/pii/B9781856172332500052).
Chinese Office Action dated Feb. 9, 2015 for Appln. No. 2012800247268.
U.S. Office Action dated Jul. 16, 2015 for U.S. Appl. No. 14/077,903.
Chinese Office Action dated Jun. 30, 2015 for Appln. No. 2012800400535.
Chinese Office Action dated Jul. 22, 2015 for Appln. No. 2012800400501.
Chinese Office Action dated Nov. 1, 2015 for Appln. No. 2012800247268.
Australian Office Action dated Oct. 21, 2015 for Appln. No. 2012271279.
Australian Office Action dated Nov. 16, 2015 for Appln. No. 2012271326.
Japanese Office Action dated Feb. 2, 2016 for Appln. No. 2014-516087.
Japanese Office Action dated Feb. 9, 2016 for Appln. No. 2014-516076.
Mexican Office Action dated Feb. 9, 2016 for Appln. No. MX/a2013/014873.
Chinese Office Action dated Apr. 7, 2016 for Appln. No. 2012800400501.
Chinese Office Action dated Mar. 22, 2016 for Appln. No. 2012800247268.
Canadian Office Action dated May 10, 2016 for Appln. No. 2835225.
Chinese Office Action dated Jul. 19, 2016 for Appln. No. 2012800236808.
Japanese Office Action dated Jul. 5, 2016 for Appln. No. 2014-516084.
Australian Office Action dated Sep. 7, 2016 for Appln. No. 2012271279.
Acute toxicity and biodegradability of N-alkyl-N-methylmorpholinium and N-alkyl-DABCO based ionic liquids, Carlo Pretti, et al., Ecotoxicology and Environmental Safety, vol. 74, pp. 748-753, published on Nov. 18, 2010.
Study on the Synthesis of Five 1, 2-Dimethylimidazolium Type of Ionic Liquids and Their Application to Li/LiFeO4 Battery as Electrolytes; Cai et al., vol. 68, 2010, No. 10, pp. 1017-1022.
Influence of different substituent length on structure property of morpholinium ionic liquid, Chu et al, vol. 42, No. 3, Sep. 2010, pp. 108-113.
Study on the falling film characteristics of glycine ionic liquid aqueous solutions of high concentrations; Jing et al., vol. 46, No. 5, Sep. 2010, pp. 575-581.
Chinese Search Report dated Jul. 19, 2016 for Appln. No. 2012800236808.
US Office Action dated Jun. 5, 2014 of U.S. Appl. No. 13/526,058, filed Jun. 18, 2012.
US Office Action dated May 19, 2014 of U.S. Appl. No. 13/526,342, filed Jun. 18, 2012.
Yoshizawa-Fujita, M., et al., "A new Lewis-base ionic liquid comprising a mono-charged diamine structure: A highly stable electrolyte for lithium electrochemistry", Electro. Comm., vol. 8, pp. 445-449 (2006).
Stoica, D., et al., "Anionic membrane based on polyepichlorhydrin matrix for alkaline fuel cell: Synthesis, physical and electrochemical properties", Electro. Acta, vol. 53 pp. 1596-1603 (2007).
Intl. Prel. Report on Patentability dated Jan. 17, 2014 of PCT/US12/43000 filed Jun. 18, 2012.
Intl. Prel. Report on Patentability dated May 20, 2013 of PCT/US12/43013 filed Jun. 18, 2012.
Yao, C., et al., "Retention characteristics of organic compounds on molten salt and ionic liquid-based gas chromatography stationary phases", Journal of Chromatography, vol. 1216, No. 10, pp. 1658-1712 (Mar. 6, 2009).
Inti. Search Report/Written Opinion dated Sep. 5, 2012 of PCT/US2012/033940 filed Apr. 17, 2012.
Inti Search Report dated Nov. 28, 2012 of PCT/US2012/043013 dated Jun. 18, 2012.
Wang, X., et al., "A polytetrafluoroethylene-quaternanry 1,4-diazabicyclo—[2.2.2]-octane polysulfone composite membrane for alkaline anion exchange membrane fuel cells", Intl. J. Hydrogen Energy, vol. 36 No. 16, pp. 10022-10026 (May 9, 2011).
Yan, X., et al., "Quaternized poly(ether ether ketone) hydroxide exchange membranes for fuel cells", J. Membrane Science, vol. 375, No. 1, pp. 204-211 (Mar. 22, 2011).
Stoica et al., "Anionic membrane based on polyepichlorhydrin matrix for alkaline fuel cell: Synthesis, physical and electrochemical properties", vol. 53, No. 4, pp. 1596-1603 (Oct. 30, 2007).
Park, J-S., "Development of Solid-State Alkaline Electrolytes for Solid Alkaline Fuel Cells", Macromolecular Symposia, vol. 249-250, No. 1, pp. 174-182 (Apr. 1, 2007).

(56) References Cited

OTHER PUBLICATIONS

Gu, S., et al., "Soluble and Highly Conductive Ionomer for High-Performance Hydroxide Exchange Membrane Fuel Cells", Angewandte Chemie Intl. Ed., vol. 48, No. 35, pp. 6499-6501 (Aug. 17, 2009).
Inti. Search Report/Written Opinion dated Dec. 3, 2012 of PCT/US2012/043000 filed Jun. 18, 2012.
Inti Search Report/Written Opinion of PCT/US2012/042955 filed Jun. 18, 2012 dated Sep. 6, 2012.
Japanese Office Action dated Jan. 18, 2017 for Appln. No. 2014-516087.

SYNTHESIS OF HETERO IONIC COMPOUNDS USING DIALKYLCARBONATE QUATERNIZATION

CROSS REFERENCE TO RELATED APPLICATIONS

This application is a continuation of co-pending U.S. patent application Ser. No. 13/526,432, filed Jun. 18, 2012, which claims the benefit of priority to U.S. Provisional Appln. No. 61/498,308, filed Jun. 17, 2011, and 61/569,159, filed Dec. 9, 2011. The entire contents of all applications are incorporated herein by reference in their entireties.

GOVERNMENT FUNDING SUPPORT

This invention was made with U.S. government support under Contract No. DB-AR-00000038 awarded by the Department of Energy. The government has certain rights in the invention.

FIELD OF THE INVENTION

The embodiments relate to methods of making a sulfate salt of a heteroatomic compound using a dialkylcarbonate as a primary reactant. Embodiments also relate to methods of making ionic liquids by reacting the sulfate salt of a heteroatomic compound with a salt to produce an ionic liquid comprising the heteroatomic cation and the anion of the salt, or by anion exchange to produce an ionic liquid comprising the heteroatomic cation and the anion. Embodiments also relate to use of the salt made as an ionic liquid and as an additive to an alkaline electrochemical cell.

BACKGROUND OF THE INVENTION

A significant detriment to the energy density of most batteries is posed by the battery's cathode. This is true for battery chemistries using, for example, lithium or nickel. Typically, oxidant is stored at the cathode at a molar charge capacity that is two to five times lower than that of the anode. Many fuel cells, on the other hand, use oxygen from the air as a source of oxidant. The existence of a continuous and virtually limitless oxidant source enables, in principle, high energy density. However, the use of hydrogen and organic fuels precludes high energy efficiencies due to problems with vapor pressure and balance-of-systems complexity, such as humidification and membrane issues. Metal-air electrochemical cells are able to combine the ultra-high anode capacity of batteries with the air-breathing cathode of fuel cells in order to achieve substantial energy densities that are relevant to modern energy demands.

Metal-air batteries typically include a fuel electrode at which metal fuel is oxidized, an air electrode at which oxygen is reduced, and an electrolyte solution for providing ion conductivity. A limiting factor with metal-air batteries is the evaporation of the electrolyte solution, particularly the evaporation of the bulk solvent, such as water in an aqueous electrolyte solution. Because the air electrode is required to be air permeable to absorb oxygen, it is also may permit the solvent vapor, such as water vapor, to escape from the cell. Over time, the cell becomes incapable of operating effectively because of this issue. Indeed, in many cell designs this evaporation issue renders the cell inoperable before the fuel is consumed. And this issue is exacerbated in secondary (i.e., rechargeable) cells, because the fuel may be re-charged repeatedly over the life of the cell, whereas the electrolyte solution is not (absent replenishment from an external source). Also, in rechargeable cells the water solvent is typically oxidized to evolve oxygen during re-charge, which may also deplete the solution.

There are other problems associated with conventional aqueous electrolyte batteries, such as water electrolysis during recharging, and self discharge. During recharge, a current is passed through the battery to reduce the oxidized fuel at the fuel electrode. Some of the current, however, electrolyzes the water resulting in hydrogen evolution (reduction) at the fuel electrode and oxygen evolution (oxidation) at the oxygen electrode as represented in the following equations:

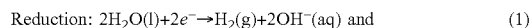

Reduction: $2H_2O(l) + 2e^- \rightarrow H_2(g) + 2OH^-(aq)$ and (1)

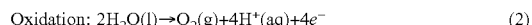

Oxidation: $2H_2O(l) \rightarrow O_2(g) + 4H^+(aq) + 4e^-$ (2)

In this manner, further aqueous electrolyte is lost from the battery. Additionally, the electrons that are consumed in reducing hydrogen are not available to reduce the fuel oxide. Therefore, the parasitic electrolysis of the aqueous electrolyte reduces the round trip efficiency of the secondary battery.

Self-discharge may result from impurities in the electrodes or reaction with the electrolyte. Typically, self-discharge from impurities in the electrodes is small (2-3% loss per month). The reaction of an active metal with water and/or $O_2$ dissolved in the water, however, may be quite high (20-30% per month).

To compensate for these problems, metal-air batteries with aqueous electrolyte solutions are typically designed to contain a relatively high volume of electrolyte solution. Some cell designs even incorporate means for replenishing the electrolyte from an adjacent reservoir to maintain the electrolyte level. However, either approach adds significantly to both the overall size of the cell, as well as the weight of the cell, without enhancing the cell performance (except to ensure that there is a sufficient volume of electrolyte solution to offset evaporation of the water or other solvent over time). Specifically, the cell performance is generally determined by the fuel characteristics, the electrode characteristics, the electrolyte characteristics, and the amount of electrode surface area available for reactions to take place. But the volume of electrolyte solution in the cell generally does not have a significant beneficial effect on cell performance, and thus generally only detracts from cell performance in terms of volumetric and weight based ratios (power to volume or weight, and energy to volume or weight). Also, an excessive volume of electrolyte may create a higher amount of spacing between the electrodes, which may increase ionic resistance and detract from performance.

Another problem that arises with alkaline electrolyte cells is the formation of filaments or dendrites during the charging/discharging cycle. For example, during the charging of a rechargeable electrochemical cell, metal cations in the electrolyte are reduced at the electrode and are electrodeposited onto the electrode as the metal. Ideally, the electrodeposited metal is laid down as a smooth layer over the entire electrode surface, thereby preserving the electrode surface morphology from one discharge-charge cycle to the next. In practice, however, the metal tends to deposit preferentially at certain sites on the electrode. As a consequence, the morphology of the metal deposit is such that the electrode surface undergoes modification ranging from moderate roughening to formation of a coating of filaments or dendrites over the entire surface. After several cycles, the electrode can become covered by a dense mat of interwoven dendrites. This type of metal deposition is undesirable and also hazardous in electrochemical cells because the metal dendrites are often small enough to penetrate the microporous materials that are conventionally used to separate the anode from the cathode current collector. As a consequence, the dendrites can grow through the separator material and cause a short-circuit between the electrodes, resulting in cell failure and possible explosion. Dendrite growth around the edges of the separator material can also occur with similar results.

The use of non-aqueous systems for electrochemical cells has been suggested (see, e.g., U.S. Pat. No. 5,827,602). In non-aqueous systems, the aqueous electrolyte may be replaced with an ionic liquid. Ionic liquids which contain a strong Lewis acid such as $AlCl_3$, however, are known to liberate toxic gases when exposed to moisture.

The use of low or room temperature ionic liquid rather than an aqueous electrolyte in a metal-air electrochemical cell, as described in U.S. Provisional Application Ser. No. 61/383,510, filed Sep. 16, 2010; 61/355,081, filed Jun. 15, 2010; 61/334,047, filed May 12, 2010; 61/329,278, filed Apr. 29, 2010; 61/177,072, filed May 11, 2009, and 61/267,240, filed Dec. 7, 2009, and described in U.S. patent application Ser. No. 13/105,794, filed on May 11, 2011; Ser. No. 13/096,851, filed Apr. 28, 2011; Ser. No. 13/085,714, filed Apr. 13, 2011; and Ser. No. 12/776,962, filed May 10, 2010, the disclosures of each of which are incorporated herein by reference in their entirety. The use of a low or room temperature ionic liquid in the cell essentially eliminates the problems associated with evaporation of solvent from an electrolytic solution.

Room temperature ionic liquids have extremely low vapor pressures (some have vapor pressures that are essentially immeasurable under standard conditions) and thus experience little or no evaporation. Therefore, cells using low or room temperature ionic liquids as their ionically conductive media need not incorporate excessive volumes of solution in order to compensate for evaporation over time. Relatively small amounts of ionic liquid are sufficient to support the electrochemical reactions needed for cell operation, thereby reducing cell weight and volume and increasing power to volume/weight ratios. Also, other problems associated with solvents, such as hydrogen evolution in an aqueous solution, may be avoided. This development is not conceded to be prior art and merely is described for contextual purposes to facilitate an understanding of the further development described herein.

Quaternization of tertiary amines, especially imidazole compounds and linear amines, by reaction with dimethyl carbonate is known. Some describe the use of the carboxylates or carbonates produced by this reaction as useful ionic liquid intermediates. See, e.g., Holbrey, et al., "1,3-Dimethylimidazolium-2-carboxylate: the unexpected synthesis of an ionic liquid precursor and carbine-$CO_2$ adduct," Chem. Commun. (2003), 28-29; Smiglak, et al., "Ionic Liquids via reaction of the zwitterionic 1,3,-dimethylimidazolium-2-carboxylate with protic acids, . . . " Green Chem., Vol. 9, pp. 90-98 (2006); Bridges, et al., "An Intermediate for the Clean Synthesis of Ionic Liquids . . . ," Chem. Eur. J., 5207-5212 (2007); Holbrey, et al., "Optimized microwave-assisted synthesis of methylcarbonate salts; . . . ," Green Chem., Vol. 12, pp 407-413 (2010); Yang, et al., "Dimethyl Carbonate Synthesis catalyzed by DABCO-derived basic ionic liquids via transesterification of ethylene carbonate with methanol," Tetrahedron Letters, 51, pp 2931-2934 (2010); and U.S. Pat. Nos. 4,892,944, and 5,865,513, the disclosures of each of the U.S. patents is incorporated by reference herein in its entirety.

SUMMARY

One feature of an embodiment provides a method for preparing a sulfate salt of a heteroatomic compound comprising reacting a heteroatomic compound with an excess of diaklycarbonate to produce a quaternized heteroatomic compound containing an alkyl group, and an alkyl carbonate ion; and acidifying the product of that reaction to produce a bisulfate salt of the heteroatomic compound. An additional feature of the embodiments provides a method for converting the bisulfate salt of the heteroatomic compound to an ionic liquid comprising an alkyl-heteroatomic cation and an anion.

Another feature of an embodiment provides an electrochemical metal-air cell comprising a fuel electrode for oxidizing a metal fuel; an air electrode for absorbing and reducing gaseous oxygen; and an ionically conductive medium comprising a low temperature ionic liquid having a melting point at or below 150° C. at 1 atm, wherein the ionic liquid comprises a cation of the heteroatomic compound and an anion prepared in accordance with the method described above. The ionic liquid is contained in a space between the fuel electrode and the air electrode for conducting ions for supporting the electrochemical reactions at the fuel and air electrodes.

Another feature of an embodiment provides an electrochemical cell comprising a cathode, an anode, an aqueous electrolyte and an additive that includes a heteroatomic compound cation and an anion (hetero ionic compound or complex).

For the purposes of this application, a low temperature ionic liquid is defined as an ionic liquid having a melting point at or below 150° C. at 1 atm. These low temperature ionic liquids may also include the species known as room temperature ionic liquids, which are defined as ionic liquids having a melting point at or below 100° C. at 1 atm. Ionic liquids are also referred to as liquid salts. By definition, an ionic liquid is composed primarily of anions and cations of the salt. While an ionic liquid itself may be a solvent with respect to one or more other soluble products present in the ionic liquid, such as an additive or reactant by-product created by operation of the cell, an ionic liquid does not require the use of a solvent to dissolve the salt, as the liquid itself is "self-dissolving," i.e., it is a liquid of the electrolyte salt anions and cations by its own nature, and the use of a separate solvent to dissolve the salt is not necessary. However, the ionic liquid may in some embodiments be provided in a solvent, for example, as an additive.

However, even though low temperature or room temperature ionic liquids are defined by their respective melting points at 1 atm., in some embodiments the cell may be operated in an environment with a different pressure, and thus the melting point may vary with the operating pressure. Thus, reference to a melting point at 1 atm. is used as a reference point to define these liquids, and does not imply or restrict its actual use conditions in operation.

Other objects, features, and advantages of the present invention will become apparent from the following detailed description, the accompanying drawings, and the appended claims.

DETAILED DESCRIPTION

Figure 1:
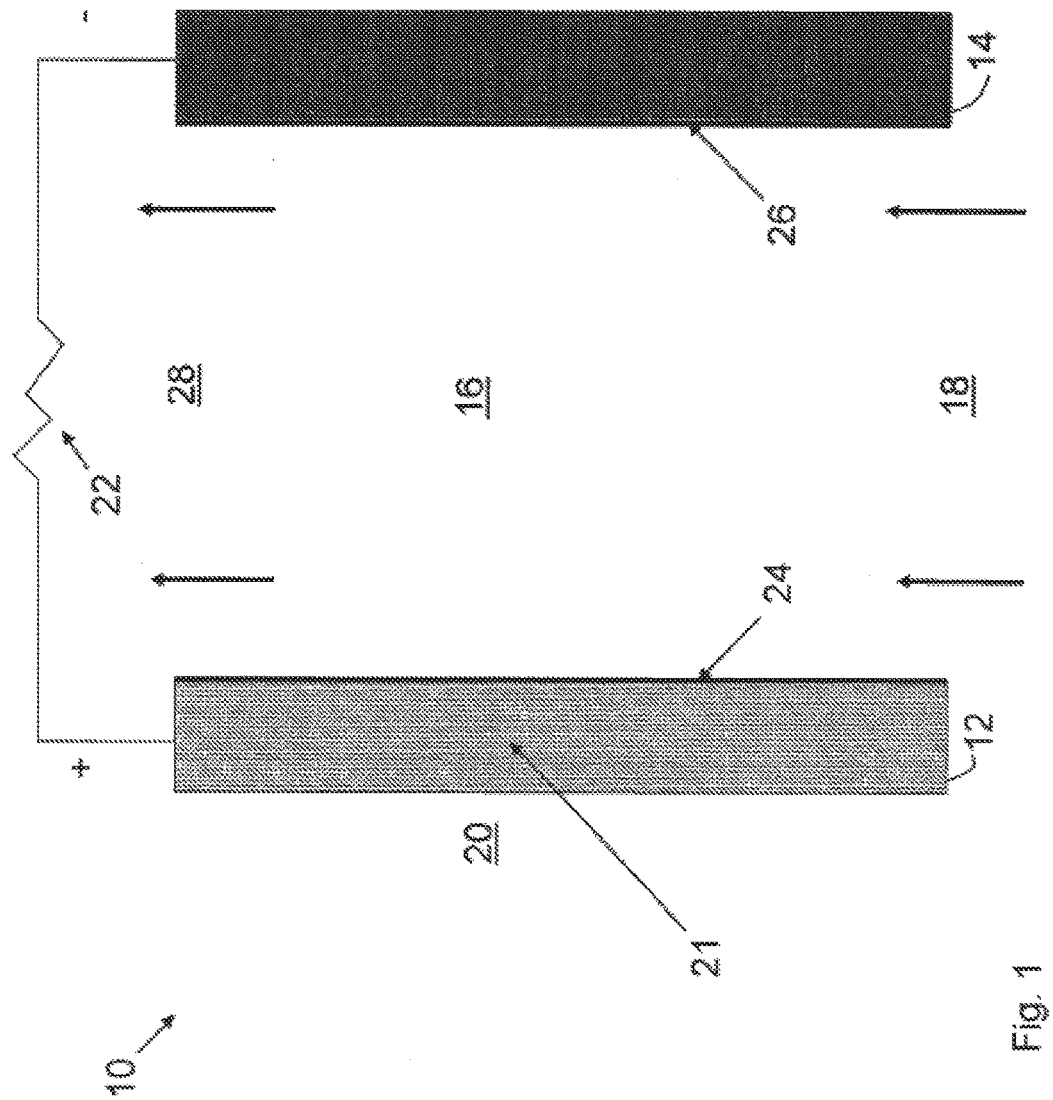
FIG. 1 is an exploded view of a cell in accordance with an embodiment of the invention.

Ionic liquids generally refer to salts that form stable liquids comprising ions. That is, ionic liquids are fully dissociated, consisting essentially of negative and positive ions. Thus, ionic liquids inherently conduct electricity. Further, ionic liquids have negligible vapor pressure, low viscosity, wide liquids (up to 400° C.), high thermal stability, and a large electrochemical window (>5V). Because of these properties, ionic liquids typically will not evaporate or be consumed during the charge/discharge cycle of an electrochemical cell.

For the purposes of this application, a low temperature ionic liquid is defined as an ionic liquid having a melting point at or below 150° C. at 1 atm. These low temperature ionic liquids may also include the species known as room temperature ionic liquids, which are defined as ionic liquids having a melting point at or below 100° C. at 1 atm. Ionic liquids are also referred to as liquid salts. By definition, an ionic liquid is composed primarily of anions and cations of the salt. While an ionic liquid itself may be a solvent with respect to one or more other soluble products present in the ionic liquid, such as an additive or reactant by-product created by operation of the cell, an ionic liquid does not require the use of a solvent to dissolve the salt, as the liquid itself is "self-dissolving," i.e., it is a liquid of the electrolyte salt anions and cations by its own nature, and the use of a separate solvent to dissolve the salt is not needed.

However, even though low temperature or room temperature ionic liquids are defined by their respective melting points at 1 atm., in some embodiments the cell may be operated in an environment with a different pressure, and thus the melting point may vary with the operating pressure. Thus, reference to a melting point at 1 atm. is used as a reference point to define these liquids, and does not imply or restrict its actual use conditions in operation. Reference to ambient conditions refers to 1 atm. pressure and room temperature.

In some non-limiting embodiments, a substance that may be regarded in some contexts as a solvent may be added in relatively small amounts to the ionic liquid, either for enhancing the solubility of solutes in the ionic liquid, such as an additive added to or a by-product created in the ionic liquid by operation of the cell, or for providing a non-solvent functionality, such as the promotion of certain electrochemical reactions or transport of ions. Thus, the use of an ionic liquid does not entirely exclude the presence of a substance that may be regarded as solvent in other contexts, or act as a solvent with respect to solutes in the ionic liquid, but because a solvent is not needed to dissolve an ionic liquid, it can be used in a substantially smaller amount compared to conventional electrolyte salts requiring a bulk solvent for dissolution of the salt per se, such as aqueous electrolyte solutions. Indeed, in some non-limiting embodiments it is possible that no additive solvent is used.

In some non-limiting embodiments, the ionically conductive medium between the fuel and air electrodes may be a pure low temperature ionic liquid, i.e., it consists of the ionic liquid. In other non-limiting embodiments, it may consist essentially of the ionic liquid, meaning for the purposes of this application that it may include the ionic liquid and one or more other substances that do not materially affect its characteristic of being an ionic liquid. Thus, the term "consisting essentially of" an ionic liquid expressly encompasses the addition of one or more additives to enhance the ionic transport functionality of the ionic liquid, support the electrochemical reactions of the cell and/or enhance the solubility of solutes in the ionic liquid, but excludes the use of a bulk solvent required to dissolve the salt, such as is the case with aqueous electrolyte solutions. Of course, any presence of reaction by-products or ions in the ionic liquid would be permitted in either the embodiments consisting of the ionic liquid or the embodiments consisting essentially of the ionic liquid, as the very nature of the ionic liquid is to promote the transport and/or formation of such ions and/or by-products. The terms "solvent free" or "devoid of solvent" may be used to characterize the ionic liquid, and this terminology should be understood as (a) only excluding a bulk solvent that is provided for purposes of dissolving the ionic liquid, and not excluding the ionic liquid itself, which may act as a solvent with respect to another substance (e.g., an additive or the cell reaction by-products); and (b) not excluding the presence of one or more additives to enhance the ionic transport functionality of the ionic liquid, support the electrochemical reactions of the cell and/or enhance the solubility of solutes in the ionic liquid, even if such an additive theoretically could be regarded as a solvent in other contexts or with respect to solutes in the ionic liquid, but is not functioning for purposes of dissolution of the ionic liquid. For example, in some embodiments, water may be present at a level between 10 ppm and 95 wt %, or from 50 ppm and 75 wt %, or from 75 ppm and 50 wt %, or less than 50 wt % to support electrochemical reactions even though it is not functioning as a solvent with respect to the ionic liquid as it would in other types of electrolytes, namely aqueous electrolytes.

Ionic liquids generally exist in two forms: protic and aprotic. Protic ionic liquids have available protons which may be oxidized or reduced or may coordinate with negative ions, such as reduced oxygens. Some examples of protic ILs are synthesized from combinations of anions tetrachloroaluminate, bis(trifluoromethylsulfonyl)imide, methylsulfonate, nitrate, and acetate, and cations triethylammonium, diethylmethylammonium, dimethylethylammonium, dimethylethylammonium triflate, ethylammonium, α-picolinium, pyridinium, and 1,8-bis(dimethylamino)naphthalene, 2,6-di-tert-butylpyridine, and derivatives of the guanadines. Aprotic ionic liquids, however, generally do not have proton activity. Some example of aprotic room temperature ionic liquids are synthesized from combinations of anions selected from chloride (Cr), hexafluorophosphate ($PF_6^-$), iodide, tetrfluorborate, bis(trifluoromethylsulfonyl)imide ($C_2F_6NO_4S_2^-$) (TFSI), trifluoromethanesulfonate ($CF_3O_3S^-$), and cations selected from imidazolium, sulfonium, pyrrolidinium, quaternized ammonium or phosponium and their derivatives. Despite a lack of proton activity, an aprotic ionic liquid can comprise a proton. For example, an aprotic ionic liquid can comprise at least one cation that has at least one strongly bound proton thereto. Many other options of ionic liquids exist, and these lists of examples are not intended to be limiting in any way.

One embodiment includes a method of preparing a sulfate salt of a heteroatomic compound, and then converting that sulfate salt into an ionic liquid comprised of a cation of the heteroatomic compound, and an anion. The expression "heteroatomic compound" is generally known in the art, and is used herein to denote its conventional meaning, including compounds containing a heteroatom, such as a non-carbon atom. In accordance with the embodiments, however, the expression "heteroatomic compound" specifically excludes linear amine compounds and imidazoles. In one embodiment, the heteroatomic compound is not a linear heteroatomic compound. In one embodiment, a heteroatomic compound is a cyclic compound that includes a non-carbon atom, such as oxygen, nitrogen, phosphorous, or sulfur, including, but not limited to heteroaromatic compounds. In a preferred embodiment, the heteroatomic compound is a bicyclic heteroatomic compound, and most preferably the heteroatomic compound is 1,4, diazabicyclo[2,2,2] octane, commonly known as Dabco, or 1-methyl-4-aza-1-azoniabicyclo[2,2,2]octane. A preferred reaction for producing a sulfate salt of a heteroatomic compound, which is embodied in the present invention, can be represented by the following equation:

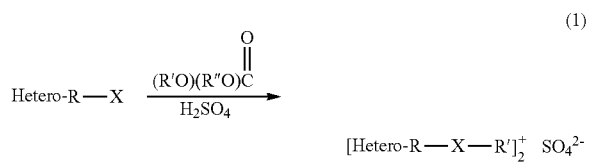

wherein Hetero-R—X is the heteroatomic compound; R, R', and R" can be the same or different and selected from hydrogen, alkyl, including but not limited to substituted and unsubstituted $C_1$-$C_{20}$ alkyl, substituted and unsubstituted aralkyl, more preferably a methyl or ethyl group; X is a heteroatom including but not limited to N, O, P, and S, which can be linear or can form a hetero or heteroaromatic ring, or bicyclic ring, with the proviso that Hetero-R—X cannot form a linear tertiary amine or an imidazole group. The positive charge on the Hetero-R—X—R' cation resides on X.

In one embodiment, the reaction route for producing a sulfate salt of a heteroatomic compound comprises: reacting a heteroatomic compound with an excess of diakylcarbonate to produce an alkylcarbonate salt of the heteroatomic compound, acidifying the alkylcarbonate salt in sulfuric acid to produce a bisulfate salt of the heteroatomic compound, optionally neutralizing the bisulfate salt to produce a sulfate salt of the heteroatomic compound, which then can be used to prepare the ionic liquid. The ionic liquid preferably can be prepared by either (a) reacting the bisulfate salt of the heteroatomic compound with a metal salt to produce an ionic liquid comprised of the cation of the heteroatomic compound and the anion of the salt; or (b) anion exchange over an anion exchange resin to produce an ionic liquid comprised of the cation of the heteroatomic compound and the anion. The advantages of this process include being halide-free; making use of dialkylcarbonates, which are powerful alkylating agents that can quaternize heteroatomic compounds that are otherwise difficult to quaternize; and producing consistent batches of the resulting ionic liquid. Other advantages, features, and objects of the embodiments will become apparent from the description of the reaction steps, examples, and the appended claims.

In one embodiment, the heteroatomic compound is selected from the group consisting of pyrrolidines, morpholines, piperidines, piperazines, quinuclidines, bicyclic amines, amidines, guanidines, alkanolamines, monoalkylamines, dialkylamines, pyrroles, pyrazoles, triazoles, thiazoles, oxazoles, pyridines, imidazopyridines, imidazopyrimidines, monoalkylphosphines, dialkylphosphines, trialkylphosphines, monoalkylphosphites, dialkylphosphites, trialkylphosphites, phosphorus monoamines, phosphorus diamines, phosphorus triamines, mercaptans, thiophenes, dihydrothiophenes, tetrahydrothiophenes, thioethers, dialkylsulfoxides, and combinations thereof. In another embodiment, the heteroatomic compound is 1,4, diazabicyclo[2,2,2] octane, commonly known as Dabco, or methyl Dabco. In another embodiment, the dialkylcarbonate is selected from the group consisting of dimethyl carbonate, diethyl carbonate, and dipropyl carbonate. In other embodiments the dialkylcarbonate includes different alkyl groups attached to the carbonate, such as methyl ethyl carbonate, methyl propyl carbonate, and the like.

The initial reaction may include reacting a heteroatomic compound with an excess of diakylcarbonate to produce an alkylcarbonate salt of the heteroatomic compound. The reaction is shown in the following equation:

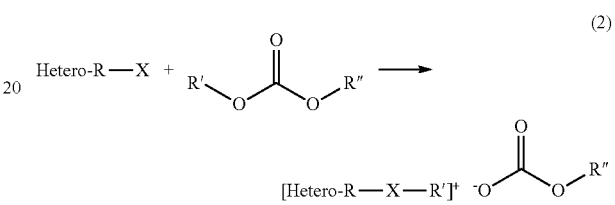

wherein Hetero-R—X is the heteroatomic compound; R, R', and R" can be the same or different and may be selected from hydrogen, alkyl, including but not limited to substituted and unsubstituted $C_1$-$C_{20}$ alkyl, substituted and unsubstituted aralkyl, more preferably a methyl or ethyl group; X is a heteroatom including but not limited to N, O, P, and S, which can be linear or can form a hetero or heteroaromatic ring, or bicyclic ring; and Hetero-R—X—R' is the resulting heteroatomic cation, with the proviso that Hetero-R—X cannot form a linear tertiary amine or an imidazole group. The positive charge on the Hetero-R—X—R' cation resides on X.

A second reaction may include acidifying the alkylcarbonate salt to produce a bisulfate salt of the heteroatomic compound, as shown in the following equation (3). Sulfuric acid is an advantageous acid, although other sulfur-containing acids could be used to produce the bisulfate salt of the heteroatomic compound.

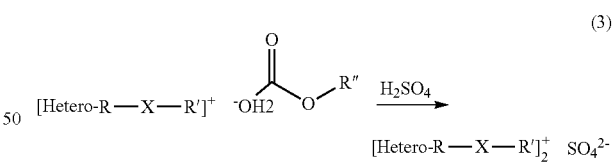

wherein Hetero-R—X is the heteroatomic compound; R, R', and R" can be the same or different and may be selected from hydrogen, alkyl, including but not limited to substituted and unsubstituted $C_1$-$C_{20}$ alkyl, substituted and unsubstituted aralkyl, more preferably a methyl or ethyl group; X is a heteroatom including but not limited to N, O, P, and S, which can be linear or can form a hetero or heteroaromatic ring, or bicyclic ring; and Hetero-R—X—R' is the resulting heteroatomic cation, with the proviso that Hetero-R—X cannot form a linear tertiary amine or an imidazole group. The positive charge on the Hetero-R—X—R' cation resides on X.

An ionic liquid comprising the heteroatomic cation formed in reaction (3) and an anion, and an additive that can be added to an electrolyte, can be prepared either by reaction with a metal salt, such as a sodium salt to produce an ionic liquid comprising the cation of the heteroatomic compound and the anion of the metal salt, or by anion exchange over an anion exchange resin (SAX). Reaction with a metal salt is shown in reaction (4) below:

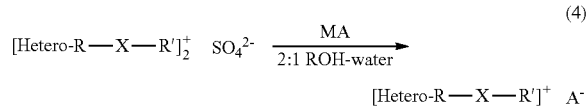

$$[\text{Hetero-R}—X—R']_2^+ \ SO_4^{2-} \xrightarrow[2:1 \ \text{ROH-water}]{MA} [\text{Hetero-R}—X—R']^+ \ A^- \quad (4)$$

wherein Hetero-R—X is the heteroatomic compound; R and R' can be selected from hydrogen, alkyl, including but not limited to substituted and unsubstituted $C_1$-$C_{20}$ alkyl, substituted and unsubstituted aralkyl, more preferably a methyl or ethyl group; X is a heteroatom including but not limited to N, O, P, and S, which can be linear or can form a hetero or heteroaromatic ring, or bicyclic ring; Hetero-R—X—R' is the resulting heteroatomic cation, with the proviso that Hetero-R—X cannot form a linear tertiary amine or an imidazole group; and MA is a salt of a desired anion, wherein M is preferably an alkali metal, an alkaline earth metal, or ammonium ($NH_4^+$), and most preferably sodium, and A is an anion. The positive charge on the Hetero-R—X—R' cation resides on X.

Exemplary anions include, but are not limited to phosphates, halophosphates, especially hexafluorophosphate, alkylphosphates, arylphosphates, nitrate, sulfate, bisulfate, carbonates, alkyl carbonates, alkylsulfates, arylsulfates, perfluorinated alkyl- and arylsulfates, sulfonate, alkylsulfonates, arylsulfonates, perfluorinated alkyl- and arylsulfonates, especially trifluoromethylsulfonate, tosylate, perchlorate, tetrachloroaluminate, heptachlorodialuminate, tetrafluoroborate, alkylborates, arylborates, amides, especially perfluorinated amides, dicyanamide, saccharinate, thiocyanate, carboxylates, acetates, preferably trifluoroacetate, and bis(perfluoroalkylsulfonyl)amide, chloride, ($Cl^-$), hydroxide ($OH^-$), hexafluorophosphate ($PF_6^-$), iodide, other halides, tetrafluoroborate, bis(trifluoromethylsulfonyl) imide ($C_2F_6NO_4S_2^-$), trifluoromethanesulfonate ($CF_3SO_3^-$; $TfO^-$), dicyanamide ($N(CN)_2^-$; dca), benzoate, acesulfame, saccharinate, and methanesulfonate. Other anions include those described in, for example, co-pending U.S. patent application Ser. No. 13/448,923, entitled: "Ionic Liquids Containing Sulfonate Ions," filed on Apr. 17, 2012, the disclosure of which is incorporated by reference herein in its entirety. These anions include, for example, isethionate ([ise]), taurinate ([tau]), 3-morpholinopropanesulfonate (MOPS), 4-(2-hydroxyethyl)-1-piperazinepropanesulfonate (HEPPS, EPPS), 1,4-piperazinediethanesulfonate (PIPES), N-(2-acetamido)-2-aminoethanesulfonate (ACES), N-cyclohexyl-3-aminopropanesulfonate (CAPS), 4-(2-hydroxyethyl)-1-piperazineethanesulfonate (HEPES), 2-[(2-hydroxy-1,1-bis(hydroxymethyl)ethyl)amino]ethanesulfonate (TES), N-[tris(hydroxymethyl)methyl]-3-aminopropanesulfonate (TAPS), 3-(N-tris[hydroxymethyl]methylamino)-2-hydroxypropanesulfonate (TAPSO), and mixtures thereof.

The reaction shown in equation 4 can be carried out in a solvent such as an alcohol, including ethanol or "reagent alcohol," which is approximately 90% ethanol, 5% isopropanol, and 5% methanol, and is sold by Fisher Scientific. Other viable solvents include methanol and tetrahydrofuran.

An ionic liquid also can be prepared by anion exchange using an anion exchange resin. In this reaction, the bisulfate salt is passed over an anion exchange resin, preferably a strong anion exchange resin (SAX). Any strong base, anion exchange resin may be used in the embodiments so long as it is capable of replacing the sulfate anion with the anion of choice, most preferably a hydroxide ion. Preferably, the anion exchange resin is a crosslinked polystyrene polymer comprising divinylbenzene (DVB) units in an amount of from about 2.5 to about 30% by weight, based on the weight of the resin. Commercially available anion exchange resins suitable for use in the embodiments include those commercially available from Siemens (e.g., A-674, A-284, A-244, A-464, and the like), Washington, D.C.; cross-linked strong base mesh anionic resins having 4% and 8% DVB crosslinking commercially available from Eichrom, Lisle, Ill.; Dowex® ion exchange resins, commercially available from The Dow Chemical Company, Midland, Mich.; strong base anion exchange resins commercially available from Resin-Tech, West Berlin, N.J. (SBACR, SBG1, SBG2, SBMP1, and the like), and mixtures thereof.

The anion exchange reaction typically takes place by passing a solution containing the heteroatomic bisulfate salt over the anion exchange resin at room temperature and pressure such that the sulfate salt remains on the resin and the anion of choice is "exchanged" and becomes associated with the heteroatomic cation. This anion-heteroatomic complex then is either used by itself as an ionic liquid, or further purified or de-watered to provide an ionic liquid suitable for use in the embodiments described herein. The anion-heteroatomic complex also can be used as an additive to an electrolyte in an electrochemical cell to suppress rough (dendritic or spongy) growth during electrodepositoin of metal in alkaline solutions, particularly highly alkaline electrolytes characteristic of alkaline batteries. Using the guidelines provided herein, coupled with the knowledge of anion exchange resins, those skilled in the art will be capable of selecting an appropriate anion exchange resin and exchange reaction conditions depending on the heteroatomic cation and desired anion.

In accordance with another embodiment, there is provided a metal-air low temperature cell and methods of making an electrochemical cell comprising an ionic liquid as prepared above as the electrolyte. In general, the method includes: (1) preparing the ionic liquid as described herein; (2) providing a first electrode, preferably an air cathode; (3) providing a second electrode, preferably a metal anode in which the second electrode is positioned apart from the first electrode thereby defining a gap therebetween; and (4) positioning the ionic liquid in the gap whereby the ionic liquid contacts both the first and second electrodes. Reference may be made to U.S. Patent Application Ser. No. 61/267,240 and Ser. No. 12/776,962 for further details concerning the construction and operation of a metal-air low temperature ionic liquid cell, the entirety of which is incorporated herein.

In accordance with another embodiment, there is provided an electrochemical cell comprising an electrode for oxidizing; an electrode for absorbing and reducing oxygen; an aqueous electrolyte and an additive that includes a cation of the heteroatomic compound and an anion prepared in accordance with the method described above. The electrolyte and additive are contained in a space between the oxidizing electrode and the reducing electrode for conducting ions for supporting the electrochemical reactions at the oxidizing and reducing electrodes.

In one embodiment, the electrochemical cell is an alkaline cell or a metal-air battery. In a metal-air battery, the metal is the fuel. That is, during discharge the metal is oxidized at the anode, providing electrons which can be used for electrical work. The oxidation reaction may be represented by the following equation:

$$\text{Metal} \rightarrow \text{Metal}^{n+}(n)e^- \quad (3)$$

The metal fuel may be of any type, and may be electrodeposited, absorbed, physically deposited, or otherwise provided on or constituting the fuel electrode. The fuel may be of any metal, including alloys or hydrides thereof, for example. For example, the fuel may comprise transition metals, alkali metals, alkali earth metals, and other or "poor" metals. Transition metals include, but are not limited to zinc, iron, manganese, and vanadium. The most common alkali metal is lithium but other alkali metals may be used. The other metals include, but are not limited to magnesium, aluminum and gallium. As used herein, the term metal fuel refers broadly to any fuel comprising a metal, including elemental metal, metal bonded in a molecule or complex, including oxides, metal alloys, metal hydrides, etc. The fuel electrode may be formed of the metal fuel as the electrode body itself in some embodiments.

The fuel electrode may have any construction or configuration. For example, the fuel electrode may be a porous structure with a three-dimensional network of pores, a mesh screen, a plurality of mesh screens isolated from one another, or any other suitable electrode. The fuel electrode includes a current collector, which may be a separate element, or the body on which the fuel is received may be electroconductive and thus also be the current collector. In an embodiment, the fuel electrode is laminated, bonded, or attached to a backing that provides the external surface of the fuel electrode. This backing may be liquid impermeable or essentially impermeable to the ionic liquid to prevent the ionic liquid from permeating outwardly through the fuel electrode via its external surface. More preferably, the backing is also impermeable to air, and particularly oxygen or other oxidant, to prevent any undesirable parasitic reaction, such as oxidant reduction in the presence of the fuel oxidation that occurs at the electrode during discharge.

Further details regarding metal fuels and fuel electrodes may be found in U.S. patent application Ser. Nos. 12/385, 217, 12/385,489, 12/885,268, 12/901,410, 12/631,484, 12/549,617, 13/019,923, 13/028,496, 61/193,540, 61/301, 377, 61/323,384, 61/329,278, 61/365,645, 61/394,954, 61/358,339, 61/383,510 and 61/243,970, the disclosures of each of which is incorporated by reference herein in their entirety.

During discharge, oxygen at the air electrode is reduced, consuming electrons. There are several possible mechanisms for oxygen reduction. The oxygen reduction reaction may occur, for example, via one of the three mechanisms discussed below. Other mechanisms, however, may occur depending on the chemical system (ionic liquid, electrode materials) chosen.

A first possible and non-limiting mechanism is a four-electron oxygen reduction reaction (ORR) where the product is a fully reduced oxygen dianion. The four-electron oxygen reduction reaction may be represented by the following equation:

$$O_2 + 2H_2O + 4e^- \rightarrow 4OH^- \quad (4)$$

Depending on the specific chemistry of the system, this reaction may form a soluble product or result locally in the formation of an insoluble metal-oxide.

In this reaction, the anions liberated may serve to mediate continued anode reaction. Relative to the other oxygen reduction mechanisms, the four-electron oxygen reduction reaction has the advantages of increased energy density and extracting the maximum number of electrons per oxygen molecule.

A second possible and non-limiting mechanism is a two-electron peroxide route. An example of this mechanism may be represented by the following equation:

$$Zn^{2+} + O_2 + 2e^- \rightarrow ZnO_2 \quad (6)$$

This mechanism has the advantage of relatively low overpotentials for the peroxide reaction. It also tends to have enhanced rechargeability relative to the first mechanism. The two-electron peroxide mechanism, however, results in lower energy density at the oxygen electrode battery relative to a four-electron process.

A third possible and non-limiting mechanism is a mixed two-electron/four-electron ORR that capitalizes on the reducing power of certain aliovalent cations. An examples of this mechanism may be represented by the following equation:

$$Mn^{2+} + O_2 + 2e^- \rightarrow MnO_2 \quad (7)$$

The nuance in this mechanism is that the product involves fully reduced $O^{2-}$ species generated by the reducing power of the aliovalent metal. In this example, $Mn^{2+}$ ends up in the $Mn^{4+}$ state on the right. This mechanism has the advantage of lower overpotentials due to reducing power of the aliovalent cation. Further, aliovalent metals may be used to make more efficient cells. The mixed two-electron/four-electron mechanism, however, results in a lower energy density battery relative to a four-electron process.

Air electrodes are typically porous structures made of polytetrafluoroethylene (PTFE) materials such as Teflon®. Preferably, the air electrode material has a high degree of solvophobicity with the electrolyte. Solvophobicity within the air electrode serves the dual roles of "wet-proofing" (i.e. preventing liquid electrolyte from leaving the cell) and improving access of the oxygen in the air to the oxygen reduction reaction catalyst within the porous structure. Access to the catalyst is enhanced by solvophobicity due to an increase in the triple junction line length of air-catalyst-electrolyte. The increase in the triple-junction line length reduces transport limitations. While a strong solvophobic character is advantageous, however, including solvophilic constituents in the electrode improves the tortuosity of the triple junction, improving superficial reaction site density.

FIG. 1 illustrates a low temperature ionic liquid (IL) electrochemical cell ("electrochemical cell"), generally indicated at 10, according to the embodiments of the present invention. As illustrated and described below, the electrochemical cell 10 includes a plurality of electrodes including a first electrode 12 and a second electrode 14. In other embodiments, the first electrode or the second electrode of the electrochemical cell 10 may be provided by configurations other than a single electrode. In the non-limiting embodiment illustrated in FIG. 1, the first electrode 12 is a cathode, and more specifically an air cathode, and will be referred to hereinafter as an air electrode 12. The second electrode 14 is an anode, and will be referred to hereinafter as a metal electrode 14. In an embodiment, and as described below, the electrochemical cell 10 may generate electricity by virtue of an oxidation half-reaction of a fuel at the metal electrode 14 in parallel, that is, substantially at the same time, with a reduction half-reaction of an oxidizer 20 at the air electrode 12. The illustrated embodiment is not intended to be limiting in any way.

The air electrode 12 and the metal electrode 14 preferably are spaced apart to form a gap 16 therebetween. A room temperature ionic liquid (RTIL), generally indicated at 18, may flow along the gap 16 so that the RTIL 18 may contact both the air electrode 12 and the metal electrode 14 at the same time. In an embodiment, it should be understood that the electrochemical cell 10 may be oriented in any way, and the RTIL may flow in directions other than what is illustrated. Thus, any directional references are made with regard to the orientation as shown in FIG. 1, and are not intended to limit a working embodiment to any particular orientation. In other embodiments, the RTIL 18 may be static with no flow at all. The RTIL 18 may make contact with the air electrode 12 at an air electrode/RTIL interface 24. The RTIL 18 may make contact with the metal electrode 14 at a metal electrode/RTIL interface 26. In alternative embodiments, the RTIL does not flow. That is, no mechanism for forced flow is included in the cell.

In some embodiments, the RTIL may contain water to facilitate the electrochemical reactions (discharging and charging over a number of cycles) taking place within the electrochemical cell 10. Preferably, the ionic liquid includes water in amounts of from about 15% to about 50%, more preferably from about 20% to about 40%, and most preferably from about 25% to about 30%. In electrochemical cells 10 that do not comprise a cathode and/or anode that requires water to facilitate the electrochemical reactions, it is preferred that the ionic liquids comprise less than about 25% water, more preferably less than about 20%, even more preferably less than about 15% water.

In other embodiments, water electrolysis during recharging, and self-discharge, aqueous electrolytes may be problematic for some metal air batteries. These problems not only result in a loss of electrolyte but also a reduction in the round trip efficiency of a rechargeable battery. The use of an ionic liquid electrolyte reduces or may eliminate some of these problems. Even with an ionic liquid electrolyte, however, the presence of water may cause the release of toxic gases and/or cause self-discharge. On the other hand, an ionic liquid electrolyte according to embodiments of the invention may include small amounts of water. For example, water contents of 10-100 ppm have been found to improve oxygen reduction of aprotic systems without causing unacceptable self-discharge or release of toxic gases. Consequently, some embodiments include ionic liquids prepared as described herein, in which the ionic liquids contain anywhere from about 5 to about 100,000 ppm water, more preferably from about 7 to about 1,000 ppm water, and most preferably from about 10 to about 100 ppm water. Those skilled in the art will be capable of determining the appropriate amount of water to include in the RTIL prepared in accordance with the embodiments, depending on the particular cell configuration, and using the guidelines provided herein.

As alluded to above, a reduction half-reaction may take place at the air electrode 12. In an embodiment, an oxidizer 20 may be reduced through the reduction half-reaction at the air electrode 12. For non-limiting illustration purposes, the electrons from the metal electrode 14 may flow to an external circuit 22 (i.e., a load) and return to the air electrode 12 to facilitate the reduction of the oxidizer 20. The oxidizer 20 is reduced on the air electrode 12 at oxidizer reduction reaction sites 21. In an embodiment, a catalyst is used to facilitate the oxidizer reduction half-reaction at the oxidizer reduction reaction sites 21. The air electrode 12 may include catalyst material, such as manganese oxide, nickel, pyrolized cobalt, activated carbon, silver, platinum, or any other catalyst material or mixture of materials with high oxygen reduction activity for catalyzing reduction of the oxidizer, which will be discussed below. In an embodiment, the air electrode 12 may be porous and the porous body with a high surface area may comprise the catalyst material.

In an embodiment, the air electrode 12 may be a passive or "breathing" air electrode 12 that is passively exposed, such as through windows or openings to an oxidizer source (typically oxygen present in ambient air) and absorbs the oxidizer 20 for consumption in the electrochemical cell 10 reactions. That is, the oxidizer 20, will permeate from the oxidizer source into the air electrode 12. Thus, the oxidizer 20 need not be actively pumped or otherwise directed to the air electrode 12, such as via an inlet. Any part of the air electrode 12 by which the oxidizer 20 is absorbed or otherwise permeates or contacts the air electrode 12 may be generically referred to as an "input." The term input may broadly encompass all ways of delivering oxidizer to the air electrode 12 for the oxidizer reduction half-reaction at the oxidizer reduction reaction sites 21 on the air electrode 12.

By means of a non-limiting illustration, the air electrode 12 may be a gas permeable electrode having an outer surface exposed to ambient air such that the oxidizer 20 comprises oxygen that permeates the air electrode 12. Similarly, the air electrode 12 may comprise a barrier membrane on the outer surface of the air electrode 12 that is gas permeable and liquid impermeable so as to permit permeation of the oxidizer 20 via the outer surface of the air electrode 12 and prevent the RTIL 18 from flowing through the outer surface of the air electrode 12. In an embodiment, the air electrode 12 may be a porous body covered on the inner side by a liquid permeable layer through which the RTIL 18 may pass through so that the low temperature IL 18 may contact the porous body.

The relationship between the RTIL 18 and the air electrode 12 may impact the overall energy density of the electrochemical cell 10. For that reason, the vapor pressure and surface tension characteristics of the RTIL 18 in view of the air electrode 12 should be carefully selected. For instance, in an embodiment, the air electrode 12 may repel the RTIL so that it may prevent the RTIL 18 from wicking, that is, flowing in a capillary-like manner through the air electrode 12. In another embodiment, the air electrode 12 may be designed with porosity to absorb the RTIL so that it exposes the RTIL to more air electrode 12 surface area for purposes of enabling the desired electrochemical reactions at the air electrode 12. The air electrode 12 may support catalyst decoration at the oxidizer reduction reaction sites 21 to improve the efficiency of the reaction. In an embodiment, the catalyst may be decorated with metal ions which may enhance the activity of the catalyst in catalyzing the oxidizer reduction reaction at the oxidizer reduction reaction sites 21 on the air electrode 12. The air electrode 12 may have a high ionic conductivity to provide reactants and remove products of the oxidizer reduction reaction from the air electrode 12. In an embodiment, the air electrode 12 may have high electrical conductivity character to carry electrons from the external load 22 to the oxidizer reduction reaction sites 21. The air electrode 12 and RTIL 18 characteristics may be further defined.

In an embodiment, the metal-oxide by-products 28 may be formed at the metal electrode 14. Whereas reduced oxidizer ions in an aqueous electrolyte coordinate, that is, donate electrons to water molecules to form water, peroxides and/or hydroxides, and thereby increase problems with vapor pressure and corrosion, in this non-limiting embodiment, the RTIL 18 may promote both the oxidizer reduction reaction at the air electrode 12 and the conduction of the reduced oxidizer ions to the metal electrode 14. In support of this result, the RTIL 18 may contain soluble species that interact with the reduced oxidizer ions, with the RTIL 18 typically being protic. The RTIL 18 may also support the reduced oxidizer ions as they migrate to the metal electrode 14. By means of a non-limiting illustration, the migration of the reduced oxidizer ions may refer to transport of the reduced oxidizer ions via convection transport, or conduction transport or diffusion transport. The RTIL 18 may also support the oxidized metal-fuel ions remaining at the metal electrode 14. In doing so, the RTIL 18 promotes the reaction between the reduced oxidizer ions and the oxidized metal-fuel ions to produce the metal-oxide by-products 28. In an embodiment, the metal-oxide by-products 28 may be stored at the metal electrode 14. In an embodiment where the metal-oxide by-product 28 is stored at the metal electrode 14, this embodiment is best used as a primary (i.e., non-rechargeable) battery, as the oxygen is stored at the metal electrode 14 and is not locally available to an oxygen evolving electrode for oxidation of the reduced oxygen species.

The storage of the metal oxide locally at the air electrode is facilitated by the air electrode 12 having a pore size in at least the regions contacting the ionic liquid sufficient to contain the oxide within the air electrode 12 body. That is, the pore size may be dependent on the size of the oxide. A network of such pores may increase the storage capacity of the air electrode 12.

In an embodiment, the oxidizer source is ambient air, and the oxidizer 20 is oxygen. In an embodiment, oxygen as the oxidizer 20 may be reduced at the air electrode 12 to form reduced oxygen ions. In an embodiment, the oxygen may be supplied from an evolved oxygen recovery system used in a regenerative electrochemical cell. Other examples of electrochemical cells that may be useful embodiments of the invention herein are shown, for example, in U.S. patent application Ser. No. 12/549,617, filed on Aug. 28, 2009, which is incorporated herein by reference in its entirety.

The electrolytes of the present invention may be used in other cell configurations. An alternate cell configuration, for example, comprises a compact wound cell illustrated in U.S. Patent Application No. 61/267,240 and Ser. No. 12/776,962, hereby incorporated by reference in their entirety.

The hetero ionic complex prepared using dialkyl quaternization may be used in a metal-air cell described above as an additive to be used together with a conventional alkaline electrolyte. The hetero ionic complex also may be used in a conventional alkaline cell as an additive for the electrolyte. In this embodiment, it is not necessary, although possible, that the heteroatomic compound exclude linear tertiary amines and imidazoles.

Figure 2:
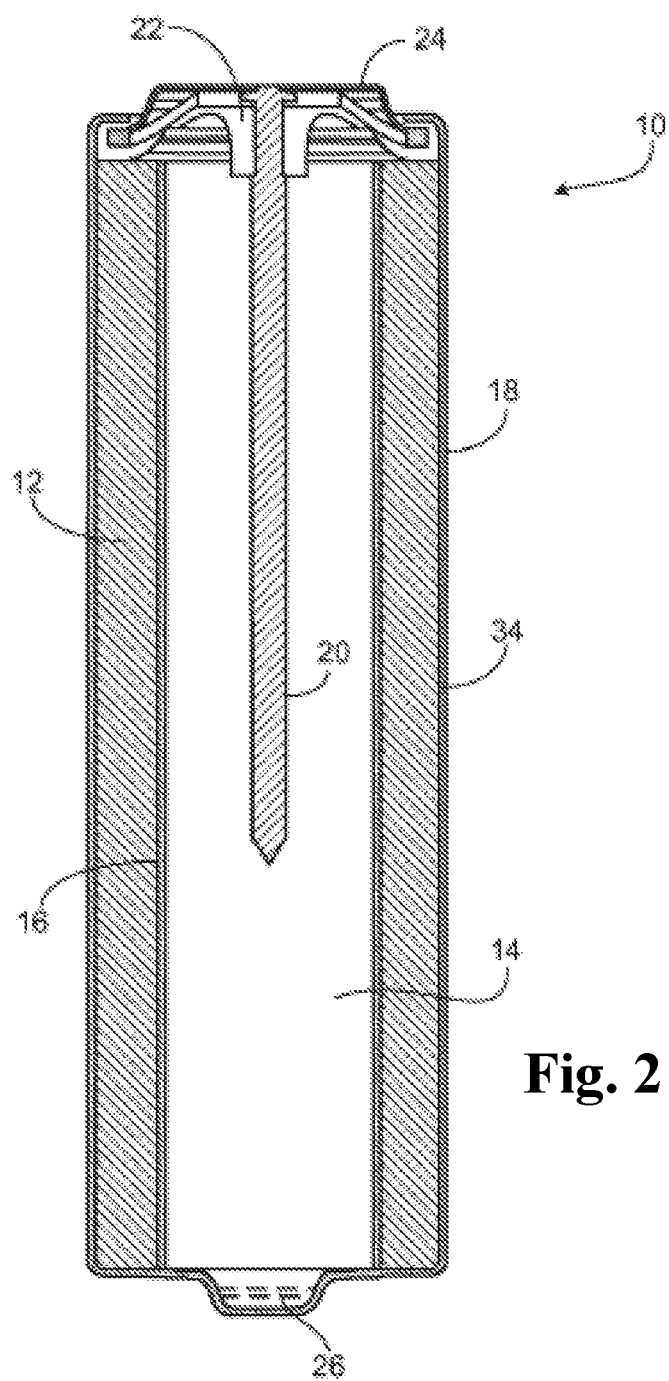
FIG. 2 is a schematic of an exemplary alkaline cell in accordance with an embodiment.

A typical alkaline cell is illustrated in FIG. 2. Referring to FIG. 2, battery 10 includes a cathode 12, an anode 14, an optional separator 16 and a cylindrical housing 18. Separator 16 is optional in certain embodiments, and in other embodiments, no separator is used. Battery 10 also includes current collector 20, seal 22, and a negative metal end cap 24, which serves as the negative terminal for the battery. A positive pip 26, which serves the positive terminal of the battery, is at the opposite end of the battery from the negative terminal. An electrolytic solution is dispersed throughout battery 10. Battery 10 can be an alkaline battery, for example, an AA, AAA, AAAA, C, or D battery.

Cathode 12 may include one or more cathode active materials, carbon particles, and a binder. The cathode may also include other additives. In order to minimize cell distortion while maintaining good cell performance, the cathode porosity should be between about 22% and about 31%, preferably between about 25.5% and about 28.5%. Examples of cathode active materials include manganese dioxide, nickel oxyhydroxide, iron disulfide, silver oxide, or copper oxide.

An electrolyte solution can be dispersed throughout cathode 12, and the electrolyte can be an aqueous solution of alkali hydroxide, such as potassium hydroxide or sodium hydroxide. The electrolyte also may be comprised of an aqueous solution of saline electrolyte, such as zinc chloride, ammonium chloride, magnesium perchlorate, magnesium bromide, or their combinations.

Anode 14 can be formed of an anode active material, a gelling agent, and minor amounts of additives, such as gassing inhibitors. In addition, a portion of the electrolyte solution discussed above may be dispersed throughout the anode. Examples of the anode active material include zinc. Preferably, to compensate for the increased active material in the cathode, the anode active material includes zinc having a fine particle size, e.g., an average particle size of less than 175 microns. The use of this type of zinc in alkaline cells is described in U.S. Pat. No. 6,521,378, the complete disclosure of which is incorporated herein by reference. The zinc loading also tends to affect the degree of cell distortion, with higher loadings tending to cause increased swelling of the anode. Preferably, the zinc loading in the zinc slurry used to manufacture the anode is from about 64% to about 69%, more preferably from about 66% to 68%.

Examples of suitable gelling agents can include a polyacrylic acid, a grafted starch material, a salt of a polyacrylic acid, a carboxymethylcellulose, a salt of a carboxymethylcellulose (e.g., sodium carboxymethylcellulose) or combinations thereof. The anode further may include a gassing inhibitor that can include an inorganic material, such as bismuth, tin, or indium. Alternatively, the gassing inhibitor can include an organic compound, such as a phosphate ester, an ionic surfactant or a nonionic surfactant.

Separator 16 can be a conventional alkaline battery separator. Preferably, the separator material is thin. For example, for an AA battery, the separator may have a wet thickness of less than 0.30 mm, preferably less than 0.20 mm and more preferably less than 0.10 mm, and a dry thickness of less than 0.10 mm, preferably less than 0.07 mm and more preferably less than 0.06 mm. The basis weight of the paper is generally in the range of about 20 to 80 g/m.sup.2. In some preferred implementations the paper has a basis weight of 35 g/m$^2$ or less. In other embodiments, separators 16 and 42 can include a layer of cellophane combined with a layer of non-woven material. The separator also can include an additional layer of non-woven material.

In some implementations, the separator is wrapped about a mandrel to form a tube. In such cases, it is generally preferred that the number of wraps of the separator is an integer or "whole number" (e.g., 1, 2, 3, 4 . . . ), rather than a fractional number (e.g., 1.25). When the number of wraps is an integer, the cell discharge around the cell circumference tends to be more uniform than if the number of wraps contains a fractional amount. Due to practical limitations on manufacturing, it may not be possible to obtain exactly integral (whole number) wraps, however it is desirable to be as close to integral as possible, e.g., 0.8 to 1.2, 1.8 to 2.2, 2.8 to 3.2, etc. Separator designs of this kind will be referred to herein as having "substantially integral wraps."

Housing 18 can be a conventional housing commonly used in primary alkaline batteries, for example, nickel plated cold-rolled steel. Current collector 20 can be made from a suitable metal, such as brass. Seal 22 can be made, for example, of a polyamide (Nylon).

A problem that may arise with such alkaline electrolyte cells is the formation of filaments or dendrites during the charging/discharging cycle. For example, during the charging of a rechargeable electrochemical cell, metal cations in the electrolyte are reduced at the electrode and are electrodeposited onto the electrode as the metal. Ideally, the electrodeposited metal is laid down as a smooth layer over the entire electrode surface, thereby preserving the electrode surface morphology from one discharge-charge cycle to the next. In practice, however, the metal tends to deposit preferentially at certain sites on the electrode. As a consequence, the morphology of the metal deposit is such that the electrode surface undergoes modification ranging from moderate roughening to formation of a coating of filaments or dendrites over the entire surface. After several cycles, the electrode can become covered by a dense mat of interwoven dendrites. This type of metal deposition is undesirable and also hazardous in electrochemical cells because the metal dendrites are often small enough to penetrate the microporous materials that are conventionally used to separate the anode from the cathode current collector. As a consequence, the dendrites can grow through the separator material and cause a short-circuit between the electrodes, resulting in cell failure and possible explosion. Dendrite growth around the edges of the separator material can also occur with similar results.

The present inventors have discovered that the addition of a small amount of the hetero ionic complex described herein to the alkaline electrolyte can significantly reduce the formation of dendrites. A preferred hereto ionic complex for use in this regard is 1-methyl-4-aza-1-azoniabicyclo[2,2,2]octane hydroxide or alkylcarbonate (preferably methyl carbonate). The hetero ionic complex is effective at suppressing rough (dendritic or spongy) growth during electrodeposition of Zn in alkaline solutions, particularly for highly alkaline electrolytes characteristic of alkaline batteries.

Used by itself, the hetero ionic complex is believed to have a leveling and grain-refining effect, smoothing out micro-rough features on the underlying substrate. While not intended to be bound by any particular theory of operation, it is believed that the benefit may be attributed to adsorption of the cationic species and a concomitant decrease in the kinetics of the interfacial electron transfer reaction for Zn reduction. Leveling may be due to preferential adsorption of the hetero ionic complex on small protrusions, thus inhibiting Zn reduction there, while grain refining may be due to preferential adsorption at low-energy sites on the substrate. The use of the hetero ionic complex additive suppresses rough growth to (typical) Zn "thicknesses" on the order of 0.05-0.1 Ah/cm². In combination with other morphology enhancing additives (e.g. In³⁺), much thicker, compact films (up to 0.6 Ah/cm²) can be electroplated.

In one embodiment, the electrolyte is potassium hydroxide, and the additive is 1-methyl-4-aza-1-azoniabicyclo[2,2,2]octane methyl carbonate, where the additive is used in an amount sufficient to reduce the formation of dendrites on an electrode. In one embodiment, the hetero ionic complex additive is present in an amount of less than about 200 mM, or less than about 100 mM, or less than about 50 mM. In another embodiment, the hetero ionic complex is present in an amount of from about 10 to about 40 mM, or from about 15 to about 35 mM, or from about 20 to about 30 mM. These concentrations of hetero ionic complex have been found to be effective at producing smooth, compact morphologies for Zn plated from highly alkaline solutions (i.e. 6-9M KOH).

The presence of the hetero ionic complex is effective at temperatures of from about 5 to about 65° C., or from about 7 to about 50° C., or from about 10 to about 35° C., and up to current densities of 100 mA/cm². In one embodiment, the current density can be about 50 mA/cm².

The hetero ionic complex increases the activation overpotential for Zn reduction at very low current densities. The hetero ionic complex additive also has excellent chemical stability, even in highly concentrated alkaline solutions (i.e. due to Hoffmann elimination, substitution). Tests with long-running electrolytes suggest extremely low decomposition rates (based on cell performance over 1500 hrs). Electrochemical stability over a wide potential range (−1.6 to 1V vs Hg/HgO) also can be achieved in accordance with the embodiments. Moreover, the morphology is still compact after extended Zn reduction/oxidation cycling. These cycling tests show that the vast majority of the hetero ionic complex additive incorporated in the film is recovered upon subsequent stripping of the film.

Various embodiments will be described with reference to the following examples.

EXAMPLES

The following reaction sequence can be carried out to produce a variety of heteroatomic sulfate salts, which then can be converted to ionic liquids using the techniques described above. In the following reaction sequence, Hetero, R, X, R', and R" can be as described above to produce the heteroatomic sulfate salts shown in the table below.

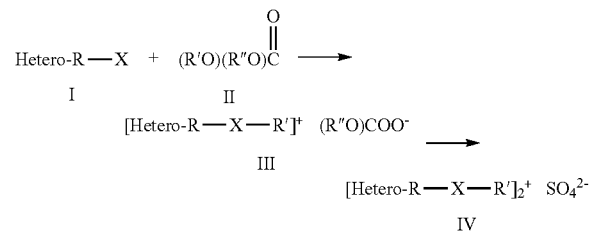

The following compounds of formula IV can be prepared using this reaction sequence.

TABLE 1

Compounds of Formula IV triethylmethylammonium sulfate

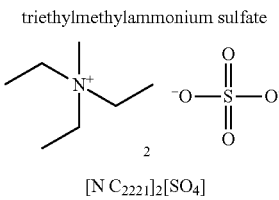

[N C₂₂₂₁]₂[SO₄]

tributylethylammonium sulfate

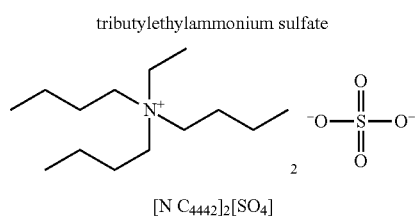

[N C₄₄₄₂]₂[SO₄]

TABLE 1-continued

Compounds of Formula IV tributylethylphosphonium sulfate

[P C$_{4442}$]$_2$[SO$_4$]

trihexylmethylphosphonium sulfate

[P C$_{6661}$]$_2$[SO$_4$]

tris(dimethylamino)methylphosphonium sulfate

[C$_1$hmpt]$_2$[SO$_4$]

tris(dimethylamino)ethylphosphonium sulfate

[C$_2$hmpt]$_2$[SO$_4$]

ethyltrimethoxyphosphonium sulfate

[P(Et)(OMe)$_3$]$_2$[SO$_4$]

ethyltrimethylsulfonium sulfate

[C$_2$dms]$_2$[SO$_4$]

trimethylsulfoxonium sulfate

[C$_1$dmso]$_2$[SO$_4$]

TABLE 1-continued

Compounds of Formula IV

N-ethyl-N-methylpyrrolidinium sulfate

[C$_2$mpy]$_2$[SO$_4$]

N-butyl-N-methylpyrrolidinium sulfate

[C$_4$mpy]$_2$[SO$_4$]

N-ethyl-N-methylmorpholinium sulfate

[C$_2$nmm]$_2$[SO$_4$]

N-butyl-N-methylmorpholinium sulfate

[C$_4$nmm]$_2$[SO$_4$]

N-ethyl-N-methylpiperidinium sulfate

[C$_2$mpp]$_2$[SO$_4$]

N-ethyl-N,N'-dimethylpiperazinium sulfate

[C$_2$dmpz]$_2$[SO$_4$]

N-ethyl-N-methylthiomorpholinium sulfate

[C$_2$nmtm]$_2$[SO$_4$]

TABLE 1-continued

Compounds of Formula IV

N-ethyl-N-methylthiomorpholinium-4,4-dioxide sulfate

[C₂nmtmO₂]₂[SO₄]

S-ethyl-1,4-thioxanium sulfate

[C₂thx]₂[SO₄]

S-ethyl-1,4-thioxanium-1-oxide sulfate

[C₁thxO]₂[SO₄]

1-ethyl-3-methylimidazolium sulfate

[C₂mim]₂[SO₄]

1-butyl-3-methylimidazolium sulfate

[C₄mim]₂[SO₄]

1-ethyl-2,3-dimethylimidazolium sulfate

[C₂dmim]₂[SO₄]

1-ethyl-2,3-dimethylimidazolium sulfate

[C₃dmami]₂[SO₄]

TABLE 1-continued

Compounds of Formula IV 1,3-diethyl-5-methyl-4-imidazoliummethanol sulfate

N-ethylpyridinium sulfate

[C₂py]₂[SO₄]

3-ethyl-4-methylthiazolium sulfate

[C₂4mtz]₂[SO₄]

3-ethyl-4-methyl-5-thiazoliumethanol sulfate 3-methylimidazo[1,2-a]pyridinium methylsulfate

[C₁impd]₂[SO₄]

3-methylimidazo[1,2-a]pyrimidinium methylsulfate

[C₁impm]₂[SO₄]

Methyldabconium methylcarbonate and methyldabconium sulfate can be prepared as shown in the reaction sequence below:

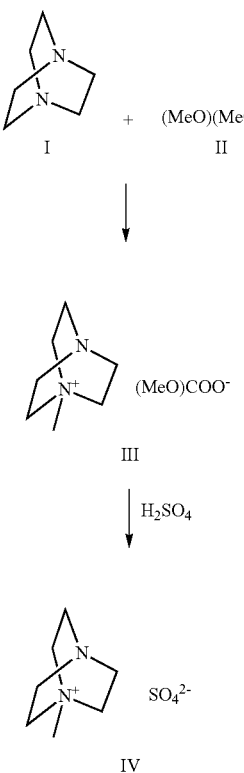

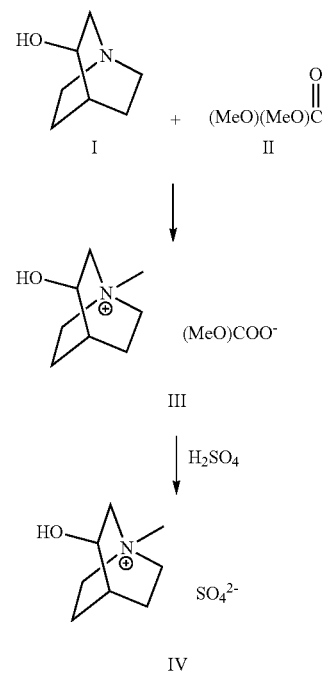

In one exemplary method, 1-methyl-4-aza-1-azoniabicyclo[2,2,2]octane or DABCO (10.024 g or 89.4 mmol) was added to dimethylcarbonate (60 mL or 712.2 mmol) available from Sigma-Aldrich, St. Louis, Mo. and mixed by a magnetic stirrer on a hot stir plate. This mixture was heated to 80° C. or vigorous reflux for 3 hours. The reaction volume was cooled to room temperature while stirring overnight. The white dabconium methylcarbonate precipitate formed and was subsequently filtered and washed with fresh dimethylcarbonate. The wet precipitate had a mass of 19.689 g (>100% yield). In yet another exemplary method, 1-methyl-4-aza-1-azoniabicyclo[2,2,2]octane (714.6 g or 6.37 mol) was dissolved in a mixture of methanol (150 mL) and dimethylcarbonate (850 mL or 1.01 mol) by overhead stirring in a jacketed reactor. The reaction was heated to 75-85° C. for 5 hours. The product methyldabconium methylcarbonate was precipitated by the addition of methylethylketone (MEK) (1750 mL) and acetone (1750 mL). The reactor was then cooled to −6° C. and held overnight. The precipitate was filtered, washed with acetone and then dried by vacuum oven. The methyldabconium methylcarbonate was recovered with a mass of 1055.4 g (5.22 mmol or 81.9% yield). The methyldabconium methylcarbonate is then acidified with sulfuric acid to produce methyldabconium sulfate.

The methyldabconium methylcarbonate salt then can be converted to an ionic liquid by reacting the sulfate salt produced above with a salt of a desired ion to produce an ionic liquid comprising the cation of the heteroatomic compound and the desired anion.

In a similar manner as above, methyl-3-quinuclidinolium methylcarbonate and methyl-3-quinuclidinolium sulfate can be prepared as shown in the reaction sequences below:

In an exemplary method, 3-quinuclidinol (10.0056 g or 78.7 mmol) was dissolved in a mixture of methanol (2 mL) and dimethylcarbonate (12 mL or 142.5 mmol) by stirring over a hot/stir plate. The reaction was heated to 75-85° C. for 5 hours. The reaction was allowed to cool to 60° C. and then the product was precipitated by the addition of methylethylketone (MEK) (25 mL) and acetone (25 mL). The methyl-3-quinuclidinolium methylcarbonate precipitate was filtered and washed with acetone and then dried by vacuum oven. The dry methyl-3-quinuclidinolium methylcarbonate powder was recovered with a mass of 15.542 g (71.3 mmol or 90.6% yield). In a similar manner, quinuclidinium salts are synthesized from quinuclidine.

In another embodiment of the method, the methylcarbonate salts above have been further processed to produce the corresponding hydroxide salt by ion exchange. In an exemplary method, dabconium methylcarbonate was dissolved in 413 g or 413 mL of water. 1.78M sulfuric acid was added to reach a final pH of 5.5. The resulting solution was passed over column of IONAC NA-38 (391.6 g) resin in the hydroxide form. The final product was 940 mL of 0.80M dabconium hydroxide solution which is 0.752 mols of product or 74.6% yield of input.

The forgoing embodiments have been provided solely to illustrate example of the present invention and should not be considered limiting. To the contrary, the present invention encompasses all modifications, substitutions, alterations, and equivalents with in the spirit and scope of the appended claims.

What is claimed:

1. An electrochemical cell comprising a cell housing, an anode, a cathode, a separator separating the anode and the cathode, and an ionically conductive medium comprising an alkaline electrolytic solution dispersed throughout the cell including the anode and the cathode, the electrolytic solution further comprising a hetero ionic complex additive comprising a heteroatomic compound cation and an anion dissolved in the electrolytic solution, wherein the cell is a secondary cell and the anode comprises a solid metal fuel for oxidation during discharging and electrodeposition thereon reduction during charging.

2. The electrochemical cell of claim 1, wherein the alkaline electrolytic solution comprises potassium hydroxide.

3. The electrochemical cell of claim 1, wherein the hetero ionic complex additive is prepared by:
   (1) reacting a heteroatomic compound with dialkylcarbonate to produce an alkylcarbonate salt of the heteroatomic compound;
   (2) acidifying the alkylcarbonate salt with a sulfate-containing acid to produce a bisulfate salt of the heteroatomic compound; and
   (3) converting the bisulfate salt of the heteroatomic compound to a hetero ionic complex comprising an alkyl-heteroatomic cation and an anion.

4. The electrochemical cell of claim 1, wherein the heteroatomic compound has the formula hetero-R—X, wherein R is selected from the group consisting of hydrogen, substituted and unsubstituted C1-C20 alkyl, and substituted and unsubstituted aralkyl, X is a heteroatom selected from the group consisting of N, O, P, S, and mixtures thereof, which can be linear or can form a hetero or heteroaromatic ring, or bicyclic ring.

5. The electrochemical cell of claim 1, wherein the heteroatomic compound is selected from the group consisting of pyrrolidines, morpholines, piperidines, piperazines, quinuclidines, bicyclic amines, amidines, guanidines, alkanolamines, monoalkylamines, dialkylamines, pyrroles, pyrazoles, triazoles, thiazoles, oxazoles, pyridines, imidazopyridines, imidazopyrimidines, monoalkylphosphines, dialkylphosphines, trialkylphosphines, monoalkylphosphites, dialkylphosphites, trialkylphosphites, phosphorus monoamines, phosphorus diamines, phosphorus triamines, mercaptans, thiophenes, dihydrothiophenes, tetrahydrothiophenes, thioethers, dialkylsulfoxides, and combinations thereof.

6. The electrochemical cell of claim 4, wherein the heteroatomic compound is 1,4, diazabicyclo[2,2,2] octane.

7. The electrochemical cell of claim 1, wherein the anion is selected from the group consisting of halophosphates, hexafluorophosphate, alkylphosphates, arylphosphates, nitrate, sulfate, bisulfate, carbonates, alkyl carbonates, alkylsulfates, arylsulfates, perfluorinated alkyl- and arylsulfates, sulfonate, alkylsulfonates, arylsulfonates, perfluorinated alkyl- and arylsulfonates, trifluoromethylsulfonate, tosylate, perchlorate, tetrachloroaluminate, heptachlorodialuminate, tetrafluoroborate, alkylborates, arylborates, amides, perfluorinated amides, dicyanamide, saccharinate, thiocyanate, carboxylates, acetates, trifluoroacetate, bis(perfluoroalkylsulfonyl)amide, chloride ($Cl^-$), hydroxide ($OH^-$), hexafluorophosphate ($PF_6^-$), iodide, other halides, tetrafluoroborate, bis(trifluoromethylsulfonyl)imide ($C_2F_6NO_4S_2^-$), trifluoromethanesulfonate ($CF_3SO_3^-$; $TfO^-$), dicyanamide ($N(CN)_2^-$; dca), benzoate, acesulfame, saccharinate, methanesulfonate, and mixtures thereof.

8. The electrochemical cell of claim 7, wherein the anion is an alkyl carbonate anion.

9. The electrochemical cell of claim 1, wherein the heteroatomic compound cation is 1-methyl-4-aza-1-azoniabicyclo[2,2,2]octane, and the anion is hydroxide or methyl carbonate.

10. The electrochemical cell of claim 1, wherein the heteroatomic compound cation is methyl-3-quinuclidinolium, and the anion is hydroxide or methyl carbonate.

11. The electrochemical cell of claim 1, wherein the hetero ionic complex additive is present in an amount sufficient to reduce the formation of dendrites on the cathode or anode.

12. The electrochemical cell of claim 11, wherein the hetero ionic complex additive is present in an amount of less than about 200 mM.

13. The electrochemical cell of claim 11, wherein the hetero ionic complex additive is present in an amount of from about 10 to about 40 mM.

14. An electrochemical cell comprising a cell housing, an anode, a cathode, a separator separating the anode and the cathode, and an ionically conductive medium comprising an alkaline electrolytic solution dispersed throughout the cell including the anode and the cathode, the electrolytic solution further comprising a hetero ionic complex additive comprising a heteroatomic compound cation and an anion dissolved in the electrolytic solution,
   wherein the cell is a secondary cell and the anode comprises a solid metal fuel for oxidation during discharging and reduction during charging,
   wherein the heteroatomic compound cation is 1-methyl-4-aza-azoniabicyclo[2,2,2]octane.

15. The electrochemical cell of claim 14, wherein the anion is hydroxide.

16. The electrochemical cell of claim 14, wherein the anion is an alkyl carbonate anion.

17. The electrochemical cell of claim 14, wherein the anion is methyl carbonate.

18. The electrochemical cell of claim 14, wherein the alkaline electrolytic solution comprises potassium hydroxide.

19. The electrochemical cell of claim 15, wherein the alkaline electrolytic solution comprises potassium hydroxide.

20. The electrochemical cell of claim 16, wherein the alkaline electrolytic solution comprises potassium hydroxide.

21. The electrochemical cell of claim 17, wherein the alkaline electrolytic solution comprises potassium hydroxide.

22. The electrochemical cell of claim 18, wherein the hetero ionic complex additive is present in an amount of less than about 200 mM.

23. The electrochemical cell of claim 22, wherein the hetero ionic complex additive is present in an amount of from about 10 to about 40 mM.

24. The electrochemical cell of claim 19, wherein the hetero ionic complex additive is present in an amount of less than about 200 mM.

25. The electrochemical cell of claim 24, wherein the hetero ionic complex additive is present in an amount of from about 10 to about 40 mM.

26. The electrochemical cell of claim 20, wherein the hetero ionic complex additive is present in an amount of less than about 200 mM.

27. The electrochemical cell of claim 26, wherein the hetero ionic complex additive is present in an amount of from about 10 to about 40 mM.

28. The electrochemical cell of claim 21, wherein the hetero ionic complex additive is present in an amount of less than about 200 mM.

29. The electrochemical cell of claim 28, wherein the hetero ionic complex additive is present in an amount of from about 10 to about 40 mM.

30. The electrochemical cell of claim 1, wherein the heteroatomic compound cation is an alkyl heteroatomic compound cation.

31. The electrochemical cell of claim 1, wherein the anode comprises particles of the metal fuel.

32. The electrochemical cell of claim 31, wherein the anode comprises a gelling agent.

33. The electrochemical cell of claim 31, wherein the metal fuel particles are zinc particles.

34. The electrochemical cell of claim 1, wherein the cathode comprises cathode active materials and a binder.

35. The electrochemical cell of claim 31, wherein the cathode comprises cathode active materials and a binder.

36. The electrochemical cell of claim 31, wherein the separator is selected from the group consisting of: paper, cellophane, and non-woven material.

37. The electrochemical cell of claim 35, wherein the separator is selected from the group consisting of: paper, cellophane, and non-woven material.

38. The electrochemical cell of claim 1, wherein the cell housing is cylindrical and the cathode is located between the anode and the cell housing.

39. The electrochemical cell of claim 38, further comprising a current collector extending into the anode, a negative terminal at one end of the housing connected to the current collector, and a positive terminal at an opposite end of the housing.

40. The electrochemical cell of claim 39, wherein the housing is sealed.

41. An electrochemical cell comprising a cell housing, an anode, a cathode, a separator separating the anode and the cathode, and an ionically conductive medium comprising an alkaline electrolytic solution dispersed throughout the cell including the anode and the cathode, the electrolytic solution further comprising a hetero ionic complex additive comprising a heteroatomic compound cation and an anion dissolved in the electrolytic solution,
  wherein the cell is a secondary cell and the anode comprises a solid metal fuel for oxidation during discharging and reduction during charging,
  wherein the electrolytic solution comprises at least one selected from the group consisting of potassium hydroxide, sodium hydroxide, zinc chloride, ammonium chloride, magnesium perchlorate, and magnesium bromide.

42. An electrochemical cell comprising a cell housing, an anode, a cathode, a separator separating the anode and cathode, and an ionically conductive medium comprising an alkaline electrolytic solution dispersed throughout the cell including the anode and the cathode, the electrolytic solution further comprising an additive comprising a cation of 1,4,diazabicyclo[2,2,2] octane and an anion dissolved in the electrolytic solution.

43. The electrochemical cell of claim 42, wherein the cell is a secondary cell and the anode comprises a solid metal fuel for oxidation during discharging and reduction during charging.

44. The electrochemical cell of claim 42, wherein the cation is 1-methyl-4-aza-1-azoniabicyclo[2,2,2]octane, and the anion is hydroxide or methyl carbonate.

45. The electrochemical cell of claim 43, wherein the anode comprises particles of the metal fuel.

46. The electrochemical cell of claim 45, wherein the anode comprises a gelling agent.

47. The electrochemical cell of claim 45, wherein the metal fuel particles are zinc particles.

48. The electrochemical cell of claim 43, wherein the cathode comprises cathode active materials and a binder.

49. The electrochemical cell of claim 45, wherein the cathode comprises cathode active materials and a binder.

50. The electrochemical cell of claim 45, wherein the separator is selected from the group consisting of: paper, cellophane, and non-woven material.

51. The electrochemical cell of claim 49, wherein the separator is selected from the group consisting of: paper, cellophane, and non-woven material.

52. The electrochemical cell of claim 42, wherein the cell housing is cylindrical and the cathode is located between the anode and the cell housing.

53. The electrochemical cell of claim 52, further comprising a current collector extending into the anode, a negative terminal at one end of the housing connected to the current collector, and a positive terminal at an opposite end of the housing.

54. The electrochemical cell of claim 53, wherein the housing is sealed.

55. The electrochemical cell of claim 43, wherein the cation is 1-methyl-4-aza-1-azoniabicyclo[2,2,2]octane, and the anion is hydroxide or methyl carbonate.

56. The electrochemical cell of claim 55, wherein the anode comprises particles of the metal fuel.

57. The electrochemical cell of claim 56, wherein the anode comprises a gelling agent.

58. The electrochemical cell of claim 56, wherein the metal fuel particles are zinc particles.

59. The electrochemical cell of claim 56, wherein the cathode comprises cathode active materials and a binder.

60. The electrochemical cell of claim 59, wherein the cell housing is cylindrical and the cathode is located between the anode and the cell housing.

61. The electrochemical cell of claim 60, further comprising a current collector extending into the anode, a negative terminal at one end of the housing connected to the current collector, and a positive terminal at an opposite end of the housing.

62. The electrochemical cell of claim 61, wherein the housing is sealed.

63. An electrochemical cell comprising a cell housing, an anode, a cathode, a separator separating the anode and the cathode, and an ionically conductive medium comprising an alkaline aqueous electrolytic solution dispersed throughout the cell including the anode and the cathode, the aqueous electrolytic solution further comprising a hetero ionic complex additive comprising a heteroatomic compound cation and an anion dissolved in the aqueous electrolytic solution,
  wherein the anode comprises a solid metal fuel for oxidation during discharging.

* * * * *